United States Patent
Gross et al.

(10) Patent No.: US 7,026,359 B1
(45) Date of Patent: Apr. 11, 2006

(54) UTILIZATION OF A HIGHLY FLUORINATED OLIGOMERIC ALKANE IN OPHTHALMOLOGY

(75) Inventors: Udo Gross, Berlin (DE); Dirk-Henning Menz, Diedorf (DE); Erhard Kemnitz, Berlin (DE); Hans Hoerauf, Sierksdorf (DE); Karin Kobuch, Pentling (DE)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 10/018,398

(22) PCT Filed: Apr. 27, 2000

(86) PCT No.: PCT/EP00/03817

§ 371 (c)(1),
(2), (4) Date: Mar. 22, 2002

(87) PCT Pub. No.: WO00/76491

PCT Pub. Date: Dec. 21, 2000

(30) Foreign Application Priority Data

Jun. 12, 1999 (DE) ................................ 199 26 890

(51) Int. Cl.
*A01N 29/00* (2006.01)

(52) U.S. Cl. ...................... 514/743; 514/745; 514/749; 514/912

(58) Field of Classification Search ................ 514/743, 514/745, 749, 912, 746; 424/78.04
See application file for complete search history.

(56) References Cited

U.S. PATENT DOCUMENTS

| | | |
|---|---|---|
| 4,490,351 A | 12/1984 | Clark, Jr. |
| 5,441,733 A | 8/1995 | Meinert |
| 6,040,485 A * | 3/2000 | Lattes et al. ................. 570/126 |
| 6,211,248 B1 | 4/2001 | Menz |
| 6,262,126 B1 | 7/2001 | Meinert |

FOREIGN PATENT DOCUMENTS

| | | |
|---|---|---|
| DE | 195 36 504 A1 | 4/1997 |
| DE | 198 61 012 A1 | 9/1999 |
| EP | 0 563 446 A1 | 10/1993 |
| EP | 0 877 010 A1 | 4/1998 |

OTHER PUBLICATIONS

Kobuch, K.A. et al, A New Hydrofluorocarbon with Increased Viscosity and Reduced Density for Long-Term Tamponade of the Lower Retina, IOVS, (Mar. 15, 2000), V41, #4, PS662, Meeting Info: Ann. Meeting of Assoc. of Vision & Opthalmology, Fort Lauderdale, FL, USA, Apr. 30-May 5, 2000.

Santoro, E et al, Mass Spectra of Some Partially Fluorinated Aliphatic Compounds, Org. Mass Spectrom., (1973), 7(2), 123-31.

Hoerauf, H et al, O44- A solvent for Silicone Oil Adhesions on Intraocular Lenses, Klinische Monatsblatter fur Augenheilkunde, (Feb. 1999) 241(2) 71-6.

* cited by examiner

*Primary Examiner*—Zohreh Fay
(74) *Attorney, Agent, or Firm*—Martin Fleit; Paul D. Bianco; Fleit Kain Gibbons Gutman Bongini & Bianco, P.L.

(57) ABSTRACT

The invention relates to the utilization of a highly fluorinated oligomeric alkane as a therapeutic agent in ophthalmology, the alkane having the general formula $[-R_F(CH_2)_n CR_1-CR_2-]_x$, wherein $R_F$ is a linear or branched perfluorinated alkyl chain $C_2F_5$ to $C_{12}F_{23}$, $R_1$ and $R_2$ are independently selected from the group consisting of H, $CH_3$, $C_2H_5$ and $C_3H_7$, n is selected from the numbers 0, 1 and 2, and x is a number between 2 and 6, with a molar mass of at least 750. According to the invention, a pharmacological agent is provided that is used in ophthalmology and that causes little or no damage to the retina even when used over a long period.

3 Claims, No Drawings

UTILIZATION OF A HIGHLY FLUORINATED OLIGOMERIC ALKANE IN OPHTHALMOLOGY

FIELD OF THE INVENTION

The invention concerns the utilization of a highly fluorinated oligomeric alkane in ophthalmology.

BACKGROUND OF THE INVENTION

U.S. Pat. No. 4,490,351 describes the utilization of liquid perfluorocarbons for treatment and diagnosis in ophthalmology. While such substances are used for temporary treatment of retinal detachments and as vitreous body tamponade, their long-term use, for example as vitreous body substitute, is connected with various kinds of injury to the eye. There are known side effects, for example, from perfluoropolyethers and perfluorocarbons, which are due to mechanical injuries at the retina and visual nerve, where the high density (about 1.9 g/cm$^3$) of these compounds is blamed for this.

On the other hand, partially fluorinated liquids that only have a density between 1.1 and 1.3 g/cm$^3$ and which can be used as auxiliary agents in ophthalmology for retinal unfolding, for vitreous body tamponade and as a vitreous body substitute have been proposed in the publications EP 0 563 446 A1, DE 195 36 504 A1 and DE 197 19 280 A1. These substances, too, in spite of their clearly lower densities, lead to histological changes in the region of the retina and even to the side effects that are otherwise known for perfluorinated carbons.

Finally, DE 44 05 627 A1 and EP 05 45 174 A1 describe fluorocarbon-containing oligomers of the general formula $(R_F)_x$—$R_H$ where $R_F$ means a highly fluorinated alkyl residue, which is bonded directly or via a bonding link to the $R_H$ group, which stands for an alkane residue or hydrogen and x means a number from 1 to 4, and which are prepared from compounds of the general formula Y—(CF$_2$)a-O$_b$—(CH$_2$)$_c$—CH=CH$_2$, where Y stands for a hydrogen or fluorine atom, a is a number from 2 to 16, and b and c are independently a number between 0 and 1, and d is a number between 0 and 6, with an average degree of oligomerization from 2 to 4. In said publications the described substances are described as being used as greases or lubricants and as ski base materials and also as oxygen carriers.

SUMMARY OF THE INVENTION

There is the task of providing a pharmacological agent for use in ophthalmology that causes little or no damage to the retina even when used over a long period. This task is solved through the utilization of a substance as in claim 1. Advantageous uses and embodiments can be taken from the subordinate claims.

DETAILED DESCRIPTION OF THE EMBODIMENTS

The idea underlying the invention and forming a part of the invention lies in the fact that the injurious effect of fluorocarbons when used in the eye for long periods of time is essentially caused by their ability to penetrate tissue and by the interaction of their viscosities and high densities. This is true not only when these substances are used as vitreous body substitutes in ophthalmology, but also when they are used as liquid implants, as tear substitutes and as treatment agents for the eye directly or as active agent carriers.

This idea led to the search for substances with higher viscosity with sufficiently high density and sufficient dissolving power and at the same time only minimum tissue penetration.

The tissue penetration capacity can be described qualitatively by the critical solubility temperature in hexane (abbreviation: CST). This qualitative measure of lipophilicity is at the same time a measure of the capacity for tissue penetration. While the low molecular $R_F$—$R_H$ compounds known from the prior art mentioned above in utilization for ophthalmology as a rule have CST values under −20° C., the high molecular oligomeric compounds in accordance with the invention are, in contrast, are not completely miscible with hexane until temperatures over +35° C. are reached and thus provide evidence for their insolubility or poor solubility in lipids, thus their low tissue penetration capacity. Surprisingly, in spite of this, they have a dissolving capacity for certain nonpolar substances that is higher than their monomeric analogs.

The substances in accordance with the invention, because of their particular molecular form, and in spite of their similar chemical composition to the known $R_F$—$R_H$ compounds, are not tissue-penetrating and thus suitable for long-term use in the eye, since it was recognized that the tissue-damaging properties of the known substances are due to their high penetration. It is advantageous for ophthalmological applications that the treatment agent used in accordance with the invention, because of the combination of reduced density and elevated viscosity, does not have a mechanically injurious effect in the eye and therefore can be used as a long-term vitreous body substitute. Compared to the silicone oil that is used at the present time, the utilization of the oligomers in accordance with the invention has the advantage that they can be used for coordinated oxygen therapy for the ischemic retina for a simultaneous excellent tamponade effect and can also be used in the lower segment of the eye because of the particular surface properties and their higher density than silicone oil and water.

For the same reason the utilization of the described oligomers in accordance with the invention enables various other ophthalmological applications that up to now were exclusively reserved to silicone oils. This in particular concerns the utilization as volume replacements, for example, in the form of implants. Moreover, completely new ophthalmological applications were also possible. With the utilization of the oligomers in accordance with the invention in one particularly viscous embodiment cloudy natural lenses can be replaced. Here the natural lens is extracted while maintaining the surrounding capsule, which is followed by an injection of the highly viscous oligomer into this capsule. The fluid lens materials allow retention of accommodation. Advantageously oligomers with a high degree of branching can be used for this, or the already substantially high viscosity of the oligomers can be increased even further by producing gels through the addition of certain mixtures of water and surface-active substances in accordance with known methods.

In addition, uptake of water-soluble substances into the liquid implants is enabled in this way, which considerably broadens their therapeutic applicability. Thus, with these gels applications have become possible in which it is necessary to have extremely high viscosity (fluid lenses) and mechanical stress on adjacent tissues that is as low as possible, with simultaneous absorption capacity for ions (vitreous body substitute). A really important advantage compared to the conventional fluorocarbons is that even if the gels are degraded, the remaining media can partially maintain the implant effects, since they themselves already have sufficient viscosity.

Utilization as active agent carrier is based on the possibility of dissolving pharmacological agents in the oligomers, where in particular the unusual combination of dissolving capacity on the one hand and reduced tissue penetration on the other is important. For this reason utilization as active agent carriers both in the form of volume replacements and without these application functions is of particular interest.

The advantageous physical properties like oxygen solubility as well as film-forming, but not tissue penetrating action allow other applications for the highly fluorinated oligomers, for example, as tear substitutes.

An important advantage of the described substances in view of the utilization in accordance with the invention is that they combine the known properties of fluorocarbons and silicone oil together, especially the high viscosity of silicone oil and the high density and oxygen dissolving power of fluorocarbons, namely without the toxicities that are known for other substances, for example, fluorosiloxanes or the complicated proportions that are present in mixtures of silicone oil and partially fluorinated alkanes and that limit or exclude their use as treatment agents in ophthalmology.

In addition, the oligomers, when used for ophthalmological purposes, offer the advantage that, in contrast to the silicone oils, they can be removed by simple washing since advantageous biocompatible solvents are available for the perfluorocarbons that had been mentioned for short-term use in ophthalmological practice, for example, perfluorodecalin or perfluorooctane, but also partially fluorinated alkanes such as $C_6F_{13}C_2H_5$ or $C_4F_9C_4H_9$. On the other hand, if necessary an exchange for silicone oil or vice versa can take place without the compounds mixing together.

The described oligomeric compounds have a viscous to highly viscous or even paste-like consistency and a density between 1.2 and 1.7 g/cm³. They are optically transparent with a refractive index between 1.30 and 1.45. The compounds are essentially nonpolar. However, as a peculiarity compared with the two molecular components alkane and perfluoroalkane, in isolated state there is a weak characteristic molecular polarity due to the $CF_2$—$CH_2$ group that is typical of the compounds. Physical properties like molecular weight, density, refractive index, viscosity, optical transparency and dissolving capacity can be varied according to purpose of application. This takes place through the choice of the $R_F$ and $R_H$ groups, their degree of branching and the degree of oligomerization. The physicochemical properties, however, can also be adjusted through the addition of perfluorinated or partially fluorinated alkans. The highly fluorinated oligomers are chemically and thermally extraordinarily stable and are not enzymatically degradable. They are toxicologically and dermatologically safe.

The preparation and purification of the described substances takes place in a substantially known way. For example, they are obtained as described in DE 41 39 765 or through the reaction of a branched, perfluorinated olefin with potassium or cesium fluorine in an aprotic solvent with an alkenyl halide and oligomerization with a radical initiator in a nonpolar solvent. The purification takes place, for example, by extractive and column chromatographic processes.

Some embodiment examples of a highly fluorinated oligomer are described in more detail below.

EXAMPLE 1

The highly fluorinated oligomer $(C_6F_{13}CHCH_2)_3$ is dissolved in fluorocarbons and purified via an $Al_2O_3$ chromatographic column. After removal of the solvent the last traces of volatile contaminants are removed in a vacuum. The highly fluorinated trimer according to nuclear spin resonance, infrared and mass spectroscopic tests, a uniform and highly pure substance with a molecular weight of 1055. Charging with an active agent takes place under mild conditions via a solvent that is not miscible with the trimer after distribution to saturation concentration. β-Carotene as active agent changes the color of the oligomer slightly. It is sterilized at 121° C. in an autoclave, without the physical or chemical properties of the substances being changed. The nuclear magnetic data of this substance are as follows:

$^1$H-NMR:$CH_3$:0.95 ppm; —CH—$CF_2$—:2.02 ppm; $CH_2$—:1.64 ppm $^{19}$F-NMR:$CF_3$: 82.8 ppm; —CH—$CF_2$—: 116.2 ppm; $4CF_2$—:123.2 ppm, −124.3 ppm, −124.8 ppm, −127.7 ppm $^{13}$C-NMR: $CH_3$—/$CH_2$—: 25–35 ppm $CF_3$—/$CF_2$—: 105–120 ppm.

The purity of the substance is essentially characterized by the following physical properties:

Density: 1.661 g/cm³;
Refractive index $n^D{}_{20}$: 1.3351;
Surface tension: 19.5 mN/m;
Critical solubility temperature in n-hexane, CST: 35° C.;
Viscosity: 220 mPa·sec.

This oligomer is suitable for all of the uses described above and in the claims and has the advantages mentioned above, especially in the area of long-term use.

EXAMPLE 2

72 g tridecafluoro-4,4-dimethyl-1-heptene is dissolved in 100 mL n-hexane and oligomerized with 1.7 g di-tert-butyl peroxide at 190° C. in an autoclave, resulting in a reaction mixture of a dimeric and trimeric compound. The mixture is separated by distillation, producing the trimer as a viscous colorless oil of the composition $[CF_3CF_2CF_2C(CF_3)_2 CH_2CHCH_2]_3$ with an average molecular weight of 1085 daltons. According to $^{19}$F and $^1$H NMR as well as infrared spectroscopic tests the compound corresponds to the general formula of the invention and in addition these tests confirm a high degree of purity. According to the relevant in vitro tests the highly fluorinated oil is suitable for the claimed uses.

The invention claimed is:

1. A method of treating an eye comprising the step of applying at least one highly fluorinated oligomeric compound of the general formula

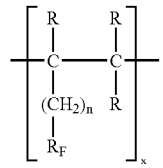

wherein
$R_F$ is a linear or branched perfluorinated alkyl chain $C_2F_5$ to $C_{12}F_{25}$, R for each position is independently selected from the group H, $CH_3$, $C_2H_5$ and $C_3H_7$, n is selected from the integers 0, 1 and 2, and x is an integer from 2 to 6, having a molecular weight of at least 750 to an eye as an ophthalmologic treating agent, wherein the application to the eye is as one of:

a) a vitreous body substitute, b) a liquid implant, c) a tear substitute, d) a carrier of a pharmacological agent mixed with the highly fluorinated oligomeric compound before applying to the eye, and e) a retina tamponade.

2. The method of claim 1 wherein a plurality of different ones of said highly fluorinated oligomeric compounds are mixed together before applying to the eye.

3. The method of claim 1 wherein said highly fluorinated oligomeric compound is a component of a pharmacological preparation that is applied to the eye.

* * * * *